United States Patent
Miyajima et al.

(10) Patent No.: US 10,226,237 B2
(45) Date of Patent: Mar. 12, 2019

(54) ULTRASONIC DIAGNOSIS APPARATUS AND ULTRASONIC PROBE

(71) Applicant: Toshiba Medical Systems Corporation, Otawara-shi (JP)

(72) Inventors: Yasuo Miyajima, Utsunomiya (JP); Hironobu Hongou, Otawara (JP); Isao Uchiumi, Nasushiobara (JP); Nobuyuki Iwama, Nasushiobara (JP); Koichi Morikawa, Nasushiobara (JP); Takatoshi Okumura, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 868 days.

(21) Appl. No.: 14/632,404

(22) Filed: Feb. 26, 2015

(65) Prior Publication Data
US 2015/0164483 A1    Jun. 18, 2015

Related U.S. Application Data

(63) Continuation of application No. PCT/JP2013/078382, filed on Oct. 18, 2013.

(30) Foreign Application Priority Data

Oct. 19, 2012  (JP) .................. 2012-231884
Oct. 18, 2013  (JP) .................. 2013-217765

(51) Int. Cl.
*A61B 8/00* (2006.01)
*A61B 8/14* (2006.01)
*A61B 8/08* (2006.01)

(52) U.S. Cl.
CPC ............... *A61B 8/546* (2013.01); *A61B 8/14* (2013.01); *A61B 8/4444* (2013.01); *A61B 8/461* (2013.01);
(Continued)

(58) Field of Classification Search
CPC .. A61B 8/546; A61B 8/00; A61B 8/58; A61B 18/1402; A61B 2018/0016;
(Continued)

(56) References Cited

U.S. PATENT DOCUMENTS

2009/0028211 A1   1/2009  Amemiya
2009/0213897 A1   8/2009  Amemiya
2014/0005546 A1*  1/2014  Haider .................. A61B 8/546
                                                    600/447

FOREIGN PATENT DOCUMENTS

CN   102631218 A    8/2012
JP   H08-56942 A    3/1996
(Continued)

OTHER PUBLICATIONS

Extended European Search Report dated Jun. 6, 2016 in Patent Application No. 13846873.1.
(Continued)

*Primary Examiner* — Elmer Chao
(74) *Attorney, Agent, or Firm* — Oblon, McClelland, Maier & Neustadt, L.L.P.

(57) ABSTRACT

An ultrasonic diagnosis apparatus includes an ultrasonic probe, an image generation unit, a display unit, and a control unit. The image generation unit generates image data from a reflected wave received from the ultrasonic probe. The display unit displays the image data. The ultrasonic probe includes a plurality of temperature sensors that measure the temperature of the ultrasonic probe and a switching circuit that is connected to the respective temperature sensors and switches connection to any one of the temperature sensors to a valid state to output data from the temperature sensors to a temperature detector. The control unit includes an instruction unit that instructs the switching circuit to switch connection to any one of the temperature sensors to a valid state at a predetermined time interval and a determination unit
(Continued)

that determines whether a temperature measured by the temperature detector is within a set temperature range.

19 Claims, 9 Drawing Sheets

(52) U.S. Cl.
CPC ............... *A61B 8/5207* (2013.01); *A61B 8/56* (2013.01); *A61B 8/58* (2013.01)
(58) Field of Classification Search
CPC ........... A61B 2018/00702; A61B 2018/00791; A61B 2018/00797
See application file for complete search history.

(56) References Cited

FOREIGN PATENT DOCUMENTS

| JP | 2004-275545 A | 10/2004 |
|---|---|---|
| JP | 2005-287755 A | 10/2005 |
| JP | 2008-188162 A | 8/2008 |
| JP | 2009-22679 A | 2/2009 |
| JP | 2009-148339 A | 7/2009 |
| WO | WO 2007/000680 A2 | 1/2007 |
| WO | WO 2008/146208 A2 | 12/2008 |

OTHER PUBLICATIONS

International Search Report dated Nov. 12, 2013 for PCT/JP2013/078382 filed on Oct. 18, 2013 with English Translation.
Written Opinion dated Nov. 12, 2013 for PCT/JP2013/078382 filed on Oct. 18, 2013.
Japanese Office Action dated Jun. 27, 2017 in Japanese Patent Application No. 2013-217765.
Corona Publishing Co., Ltd., Jan. 21, 1997, p. 38 with cover page (with partial English translation).
Combined Chinese Office Action and Search Report dated Feb. 22, 2016 in Patent Application No. 201380046863.6 (with English translation of categories of cited documents).

* cited by examiner

ULTRASONIC DIAGNOSIS APPARATUS AND ULTRASONIC PROBE

CROSS-REFERENCE TO RELATED APPLICATIONS

This application is a continuation of International Application No. PCT/JP2013/078382, filed on Oct. 18, 2013 which claims the benefit of priority of the prior Japanese Patent Application No. 2012-231884, filed on Oct. 19, 2012 and Japanese Patent Application No. 2013-217765, filed on Oct. 18, 2013; the entire contents of all of which are incorporated herein by reference.

FIELD

Embodiments described herein relate to an ultrasonic diagnosis apparatus and an ultrasonic probe.

BACKGROUND

Conventionally, in an ultrasonic diagnosis apparatus, the temperature of a surface of an ultrasonic probe that contacts a subject sometimes increases. For this reason, the ultrasonic diagnosis apparatus incorporates a temperature sensor in an acoustic module of the ultrasonic probe, and the temperature of a contact surface with the subject is monitored. When the ultrasonic diagnosis apparatus detects an abnormal increase in the temperature of the contact surface, the ultrasonic diagnosis apparatus keeps driving conditions low or stops the operation at the time of an excessive temperature increase, thereby maintaining safety of the subject.

For example, in a case of an abdomen convex probe having a wide contact surface with a subject, because a local temperature increase at an end portion of the contact surface cannot be detected only by a temperature sensor solely provided at the center, a plurality of temperature sensors are incorporated in an acoustic module. However, when wires of a probe cable and pins of probe connectors are allocated to the respective temperature sensors, the probe cable becomes large and heavy.

DETAILED DESCRIPTION

An ultrasonic diagnosis apparatus according to the present embodiment includes an ultrasonic probe, an image generation unit, a display unit, and a control unit. The ultrasonic probe transmits and receives an ultrasonic wave to and from a subject. The image generation unit generates image data from a reflected wave received from the ultrasonic probe. The display unit displays the image data. The control unit controls transmission and reception of ultrasonic waves by the ultrasonic probe. The ultrasonic probe includes a plurality of temperature sensors that measure the temperature of the ultrasonic probe and a switching circuit that is connected to the respective temperature sensors and switches connection to any one of the temperature sensors to a valid state to output data from the temperature sensors to a temperature detector. The control unit includes an instruction unit that instructs the switching circuit to switch connection to any one of the temperature sensors to a valid state at a predetermined time interval and a determination unit that determines whether the temperature measured by the temperature detector is within a set temperature range.

An ultrasonic diagnosis apparatus and an ultrasonic probe according to the present embodiments will be explained below with reference to the accompanying drawings. These embodiments can be combined to each other within a range where processing contents thereof do not contradict.

First Embodiment

Figure 1:
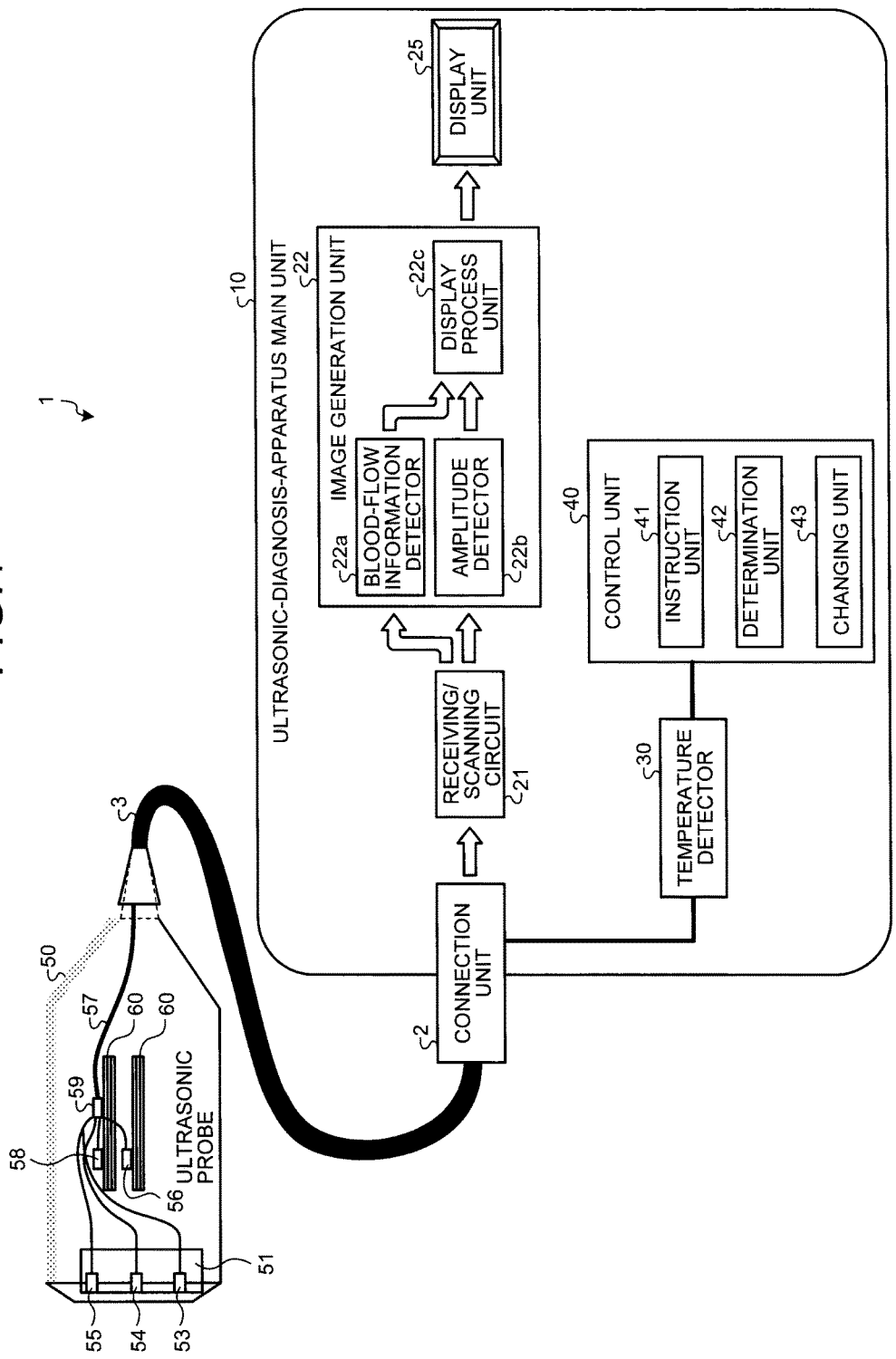
FIG. 1 is an example of a configuration of an ultrasonic diagnosis apparatus according to a first embodiment.

FIG. 1 is an example of a configuration of an ultrasonic diagnosis apparatus 1 according to a first embodiment. As shown in FIG. 1, the ultrasonic diagnosis apparatus 1 according to the first embodiment includes an ultrasonic-diagnosis-apparatus main unit 10 and an ultrasonic probe 50. The ultrasonic-diagnosis-apparatus main unit 10 is connected via a connection unit 2 and a probe cable 3 to the ultrasonic probe 50.

The ultrasonic-diagnosis-apparatus main unit 10 includes a receiving/scanning circuit 21, an image generation unit 22, a display unit 25, a temperature detector 30, and a control unit 40.

The receiving/scanning circuit 21 receives a signal having a delay added thereto in a reception circuit 80 included in the ultrasonic probe 50 that is explained later via the probe cable 3. The receiving/scanning circuit 21 further performs processes such as signal amplitude adjustment and delay addition on the received signal. The receiving/scanning circuit 21 then outputs the processed signal to the image generation unit 22.

The image generation unit 22 includes a blood-flow information detector 22a, an amplitude detector 22b, and a display process unit 22c. An output of the receiving/scanning circuit 21 is supplied to the blood-flow information detector 22a together with a reference clock. The blood-flow information detector 22a supplies an average speed (or the maximum speed), a speed distribution (or a speed distribution width), and scattering power information from a blood flow to the display process unit 22c. That is, the blood-flow information detector 22a outputs Doppler image information to the display process unit 22c.

An output of the receiving/scanning circuit 21 is supplied to the amplitude detector 22b. The amplitude detector 22b detects the magnitude of a reflected wave of an ultrasonic beam in each raster direction. The amplitude detector 22b outputs brightness information of each raster, that is, B-mode image (cross-sectional image) information to the display process unit 22c.

The display process unit 22c generates display image data from image information. In other words, while the raster of the ultrasonic probe 50 is a fan shape, the raster of the display unit 25 is horizontal as in a general television system. Therefore, the display process unit 22c performs a process of converting a raster direction (a scanning direction) of image data input from the blood-flow information detector 22a and the amplitude detector 22b, and outputs the processed image data to the display unit 25. The display unit 25 displays image data generated by the image generation unit 22.

The temperature detector 30 measures the temperature based on a signal output from a switching circuit 59 that is explained later. For example, the temperature detector 30 measures a resistance value using a signal output from the switching circuit 59 and then measures the temperature using the resistance value. The temperature detector 30 outputs the measured temperature to the control unit 40. Alternatively, a resistance value measured by the temperature detector 30 can be output to the control unit 40 and the control unit 40 can calculate the temperature using the resistance value measured by the temperature detector 30.

The control unit 40 is a control processor (CPU: Central Processing Unit) that realizes functions as an information processing device, and controls the entire processing of the ultrasonic diagnosis apparatus 1. For example, the control unit 40 controls transmission and reception of ultrasonic waves by the ultrasonic probe 50.

For example, the control unit 40 includes an instruction unit 41, a determination unit 42, and a changing unit 43, and monitors the temperature detected by the temperature detector 30. The control unit 40 is configured so as to be able to cause hardware to forcibly stop operations depending on the degree of an abnormality. Details of the instruction unit 41, the determination unit 42, and the changing unit 43 included in the control unit 40 are explained later with reference to FIG. 4.

Generally, the ultrasonic probe 50 is an electronic-scanning ultrasonic probe, and includes an acoustic module 51, temperature sensors 53 to 56, a sensor line 57, a reference sensor 58, the switching circuit 59, and an electronic circuit 60.

The acoustic module 51 is constituted by a large number of ultrasonic transducer elements that are one- or two-dimensionally arrayed. Depending on the type of the ultrasonic probe 50, the ultrasonic transducer elements are linearly arrayed or arrayed in a shape having curvature. By changing a timing of a voltage applied to each transducer element, an ultrasonic beam can be electronically scanned in a fan shape or can be focused. Further, by moving the range of used elements, the position where an ultrasonic beam is generated can be moved.

The temperature sensors 53 to 55 that detect the temperature of a contact surface with a subject are embedded in the acoustic module 51. In addition to these sensors, the temperature sensor 56 that detects the temperature of the electronic circuit 60 is also incorporated in the acoustic module 51. These temperature sensors 53 to 56 are, for example, a thermistor in which a resistance value changes depending on a change in the temperature. The reference sensor 58 is a resistor having a predetermined resistance value. In other words, the resistance value of the reference sensor 58 does not change depending on the temperature. The reference sensor 58 is used for calibrating a temperature detection system that estimates the temperature from signals output from the temperature sensors 53 to 56.

One ends of signal lines of these temperature sensors 53 to 56 and the reference sensor 58 are connected to the switching circuit 59. The switching circuit 59 is connected to one sensor line 57. The switching circuit 59 selects any one of the signal lines of the temperature sensors 53 to 56 and the reference sensor 58 and outputs a signal to the sensor line 57. The signal output from the switching circuit 59 is input via the probe cable 3 and the connection unit 2 to the temperature detector 30 within the ultrasonic-diagnosis-apparatus main unit 10. The other ends of the signal lines of the temperature sensors 53 to 56 and the reference sensor 58 are grounded.

Ultrasonic transducer elements arranged in the acoustic module 51 within the ultrasonic probe 50 are connected to a transmission circuit 70 and the reception circuit 80 included in the electronic circuit 60 to transmit and receive ultrasonic waves of the respective elements.

The transmission circuit 70 supplies a drive signal to the ultrasonic probe 50. A detailed configuration of the transmission circuit 70 is explained later with reference to FIG. 2. The reception circuit 80 adds a delay to a reflected wave signal received by the ultrasonic probe 50 and outputs the delay added signal via the probe cable 3 to the ultrasonic-diagnosis-apparatus main unit 10. As a result, the signal having a delay added thereto by the reception circuit 80 is input to the receiving/scanning circuit 21. A detailed configuration of the reception circuit 80 is explained later with reference to FIG. 3.

Figure 2:
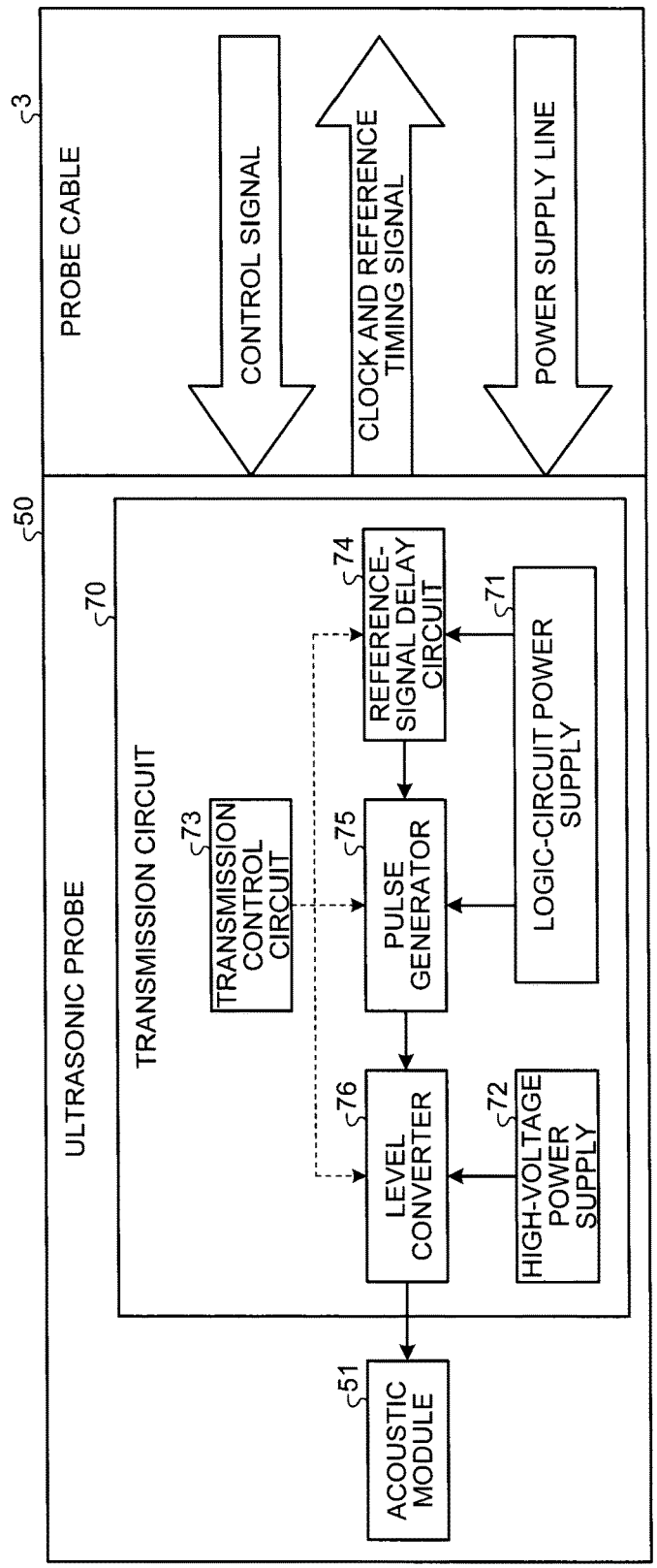
FIG. 2 is an example of a configuration of a transmission circuit according to the first embodiment.

A configuration of the transmission circuit 70 is explained with reference to FIG. 2. FIG. 2 is an example of the configuration of the transmission circuit 70 according to the first embodiment. As shown in FIG. 2, the transmission circuit 70 includes a logic-circuit power supply 71, a high-voltage power supply 72, a transmission control circuit 73, a reference-signal delay circuit 74, a pulse generator 75, and a level converter 76.

The logic-circuit power supply 71 supplies a transmission delay power supply to the reference-signal delay circuit 74. The logic-circuit power supply 71 also supplies a power supply for generating drive pulses to the pulse generator 75. The high-voltage power supply 72 supplies a high-voltage power supply that is used in the level converter 76. The power supply of the logic-circuit power supply 71 and the high-voltage power supply 72 is supplied from the probe cable 3.

The transmission control circuit 73 controls the reference-signal delay circuit 74, the pulse generator 75, and the level converter 76.

The reference-signal delay circuit 74 delays a clock and a reference timing signal that are transmitted via the probe cable 3 for every element. The reference-signal delay circuit 74 is constituted by a large number of delay lines having different delay times, and outputs of the respective delay lines are supplied to a large number of transducer elements, respectively. By changing the delay time, the direction (the raster direction) of an ultrasonic beam irradiated from the ultrasonic probe 50 can be changed to an arbitrary direction.

The pulse generator 75 supplies a drive pulse to the level converter 76 using a reference timing signal at a fixed cycle. The reciprocal of the period is a repetition frequency (a rate frequency) of an ultrasonic beam. The level converter 76 generates high-voltage pulses and supplies the pulses to elements of the acoustic module 51.

Figure 3:
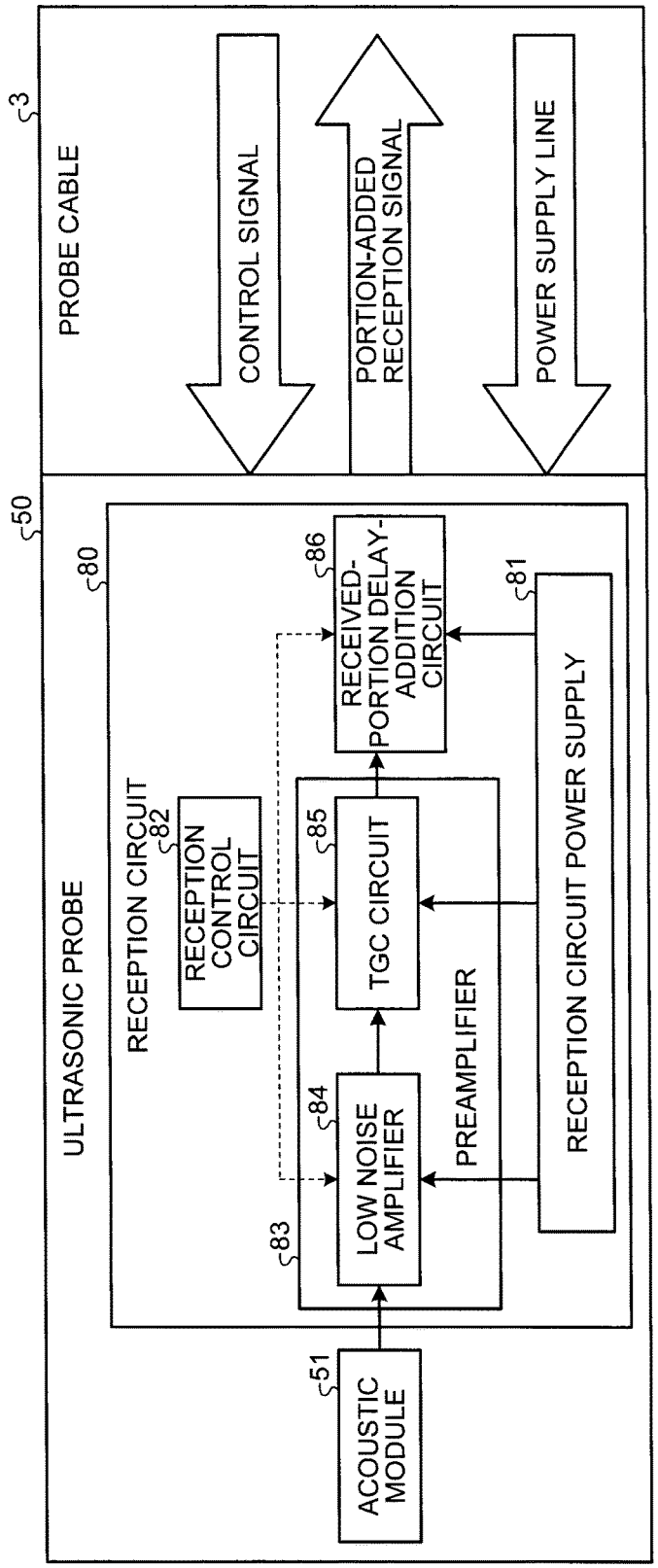
FIG. 3 is an example of a configuration of a reception circuit according to the first embodiment.

Next, a configuration of the reception circuit 80 is explained with reference to FIG. 3. FIG. 3 is an example of the configuration of the reception circuit 80 according to the first embodiment. As shown in FIG. 3, the reception circuit 80 includes a reception circuit power supply 81, a reception control circuit 82, a preamplifier 83, and a received-portion delay-addition circuit 86.

The reception circuit power supply 81 supplies a power supply to the preamplifier 83 and the received-portion delay-addition circuit 86. The reception control circuit 82 controls the preamplifier 83 and the received-portion delay-addition circuit 86.

The preamplifier 83 includes a low noise circuit 84 and a TGC (Time Gain Compensation) circuit 85, and adjusts the amplitude of a received reflected wave signal to an appropriate amplitude. The low noise circuit 84 is a low noise amplifier having a fixed amplification degree. The TGC circuit 85 changes the amplification degree during a reception period to reduce the amplification degree of a short-distance strong signal and increase the amplification degree of a long-distance weak signal. Therefore, the TGC circuit 85 prevents occurrence of practical saturation and noise characteristic degradation even when the dynamic range of the subsequent circuit is narrow.

Delays that are different for each element are given to the received-portion delay-addition circuit 86, and the received-portion delay-addition circuit 86 adds signals of a plurality of elements together. For example, the received-portion delay-addition circuit 86 adds signals of the elements so that the signals create directionality, thereby reducing the number of the signal lines. The final reception directionality is created in the receiving/scanning circuit 21. Delays of the respective elements at this time are adjusted depending on a direction that signals are desired to be received. According to the number of added elements, for example, when the number of elements is 4,000 and the number of channels of a probe cable is 200, addition is performed for every 20 elements so that the elements fall within the number of channels of the probe cable. In this way, signals are transmitted via the probe cable 3 and the connection unit 2 to the ultrasonic-diagnosis-apparatus main unit 10.

In the transmission circuit 70 within the ultrasonic probe 50, the internal temperature of the ultrasonic probe 50 increases due to a loss caused by transmission of ultrasonic waves. Furthermore, in the reception circuit 80 within the ultrasonic probe 50, the internal temperature of the ultrasonic probe 50 increases because power is consumed by a bias current. Further, also in the acoustic module 51, the temperature of the acoustic module 51 or a casing of the ultrasonic probe 50 increases due to heat generated by a loss of an transducer element, absorption of acoustic energy transmitted to a back surface by an attenuation material, a loss of acoustic energy in a substance interposed between a subject and the ultrasonic probe 50 such as rubber on an acoustic emission surface, and the like. In order to prevent the temperature from abnormally increasing and a subject and an inspector from being harmed, the temperature sensors 53 to 55 for temperature detection are provided within the ultrasonic probe 50 to monitor the temperatures.

Figure 4:
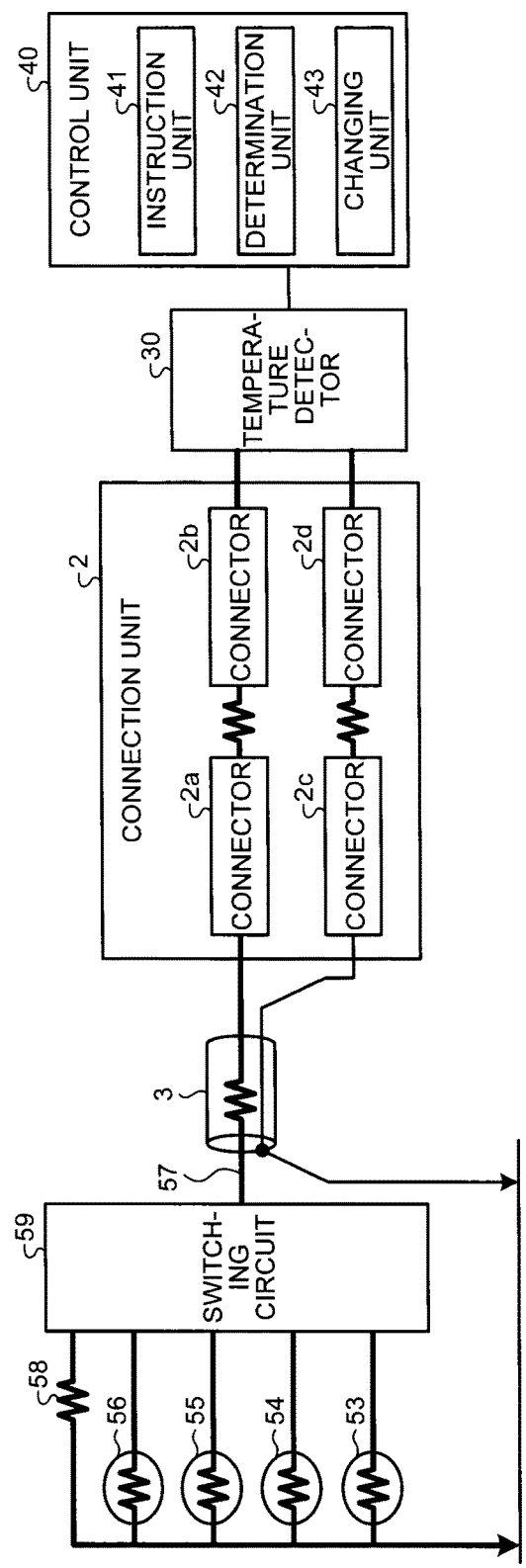
FIG. 4 is an explanatory diagram of an operation of a switching process of a sensor line by a control unit according to the first embodiment.

FIG. 4 is an explanatory diagram of an operation of a switching process of the sensor line 57 by the control unit 40 according to the first embodiment. As shown in FIG. 4, one ends of signal lines of the temperature sensors 53 to 55 that detect the temperature of the acoustic module 51, the temperature sensor 56 that detects the temperature of the electronic circuit 60, and the reference sensor 58 are commonly connected to the ground of a substrate of the electronic circuit 60. The other ends of the signal lines of the temperature sensors 53 to 56 and the reference sensor 58 are connected to the switching circuit 59.

The switching circuit 59 is connected to one sensor line 57. That is, the switching circuit 59 reduces the number of the signal lines of the temperature sensors 53 to 56 and the reference sensor 58 to one sensor line 57.

Control of the switching circuit 59 is executed by a control line connected to the ultrasonic-diagnosis-apparatus main unit 10. The switching circuit 59 validly connects a signal line of any one of the temperature sensors 53 to 56 and the reference sensor 58 that is designated by the control unit 40 to the sensor line 57. The sensor line 57 is then connected via the probe cable 3 to the connection unit 2. The ultrasonic probe 50 is connected via the connection unit 2 to the ultrasonic-diagnosis-apparatus main unit 10.

A signal line to which the signal lines of the temperature sensors 53 to 56 and the reference sensor 58 are commonly connected is also connected via the probe cable 3 to the connection unit 2. The ultrasonic probe 50 is connected via the connection unit 2 to the ultrasonic-diagnosis-apparatus main unit 10.

In the connection unit 2, there is a contact resistance between a connector 2*a* to the ultrasonic probe 50 connected to the sensor line 57 and a connector 2*b* to the ultrasonic-diagnosis-apparatus main unit 10. Further, in the connection unit 2, there is a contact resistance between a connector 2*c* to the other signal lines connected in common to the temperature sensors 53 to 56 and the reference sensor 58 and a connector 2*d* to the ultrasonic-diagnosis-apparatus main unit 10. These contact resistances are equal to or less than 1Ω in a normal state. However, in a case of bad contact due to adhesion of dust or the like, a resistance of a few ohms is generated.

In the ultrasonic-diagnosis-apparatus main unit 10, the connectors 2*b* and 2*d* are connected to the temperature detector 30. The temperature detector 30 is then connected to the control unit 40.

When any one of the temperature sensors 53 to 56 is selected, the temperature detector 30 measures the resistance value and then the temperature from the measured resistance value. The temperature detector 30 notifies the measured temperature to the control unit 40.

When the reference sensor 58 is selected, for example, when the difference between the resistance value and an expected value of the resistance value of the reference sensor is equal to or less than 1Ω, the temperature detector 30 notifies the control unit 40 that the temperature is normal. On the other hand, when the reference sensor 58 is selected, for example, when it is detected that the difference in the resistance value is a few ohms, the temperature detector 30 notifies the control unit 40 that a temperature detection system is abnormal.

As explained above, the control unit 40 includes the instruction unit 41, the determination unit 42, and the changing unit 43. The instruction unit 41 instructs the switching circuit 59 to switch connection to any one of the temperature sensors 53 to 56 and the reference sensor 58 to a valid state. For example, before scanning by the ultrasonic diagnosis apparatus 1 starts, the instruction unit 41 instructs the switching circuit 59 to switch connection to the reference sensor 58 to a valid state.

Furthermore, when it is permitted by the determination unit 42 that connection to any one of the temperature sensors 53 to 56 is switched to a valid state in a predetermined order, the instruction unit 41 instructs the switching circuit 59 to switch connection to any one of the temperature sensors 53 to 56 to a valid state in a predetermined order.

When the reference sensor 58 having a predetermined resistance value is selected, the determination unit 42 determines whether a connection state between connectors of the connection unit 2 is normal. For example, when the reference sensor 58 is selected and the determination unit 42 is notified by the temperature detector 30 that the temperature is normal, the determination unit 42 determines that a connection state between connectors of the connection unit 2 is normal. On the other hand, when the reference sensor 58 is selected and the determination unit 42 is notified by the temperature detector 30 that the temperature is abnormal, the determination unit 42 determines that a connection state between connectors of the connection unit 2 is abnormal. A case where a connection state between connectors of the connection unit 2 is normal refers to a case that connection between the switching circuit 59 and the temperature detector 30 and the control unit 40 is normal.

When a connection state between connectors of the connection unit 2 is normal, the determination unit 42 permits the instruction unit 41 to switch connection to any one of the temperature sensors 53 to 56 to a valid state in a predetermined order.

Among the temperature sensors 53 to 56, when the temperature measured by the temperature detector 30 is equal to or higher than a threshold value, the determination unit 42 determines that the temperature of the ultrasonic probe 50 is abnormal.

When it is determined by the determination unit 42 that the temperature of the ultrasonic probe 50 is abnormal, the changing unit 43 reduces power consumption of the ultrasonic diagnosis apparatus 1 lower than power consumption when it is determined that the temperature of the ultrasonic probe 50 is normal.

When it is determined by the determination unit 42 that diagnosis can be performed by the ultrasonic diagnosis apparatus 1, the changing unit 43 changes the reduced power consumption to the power consumption before the reduction. Details of a process performed by the changing unit 43 are explained later with reference to FIG. 5.

Figure 5:
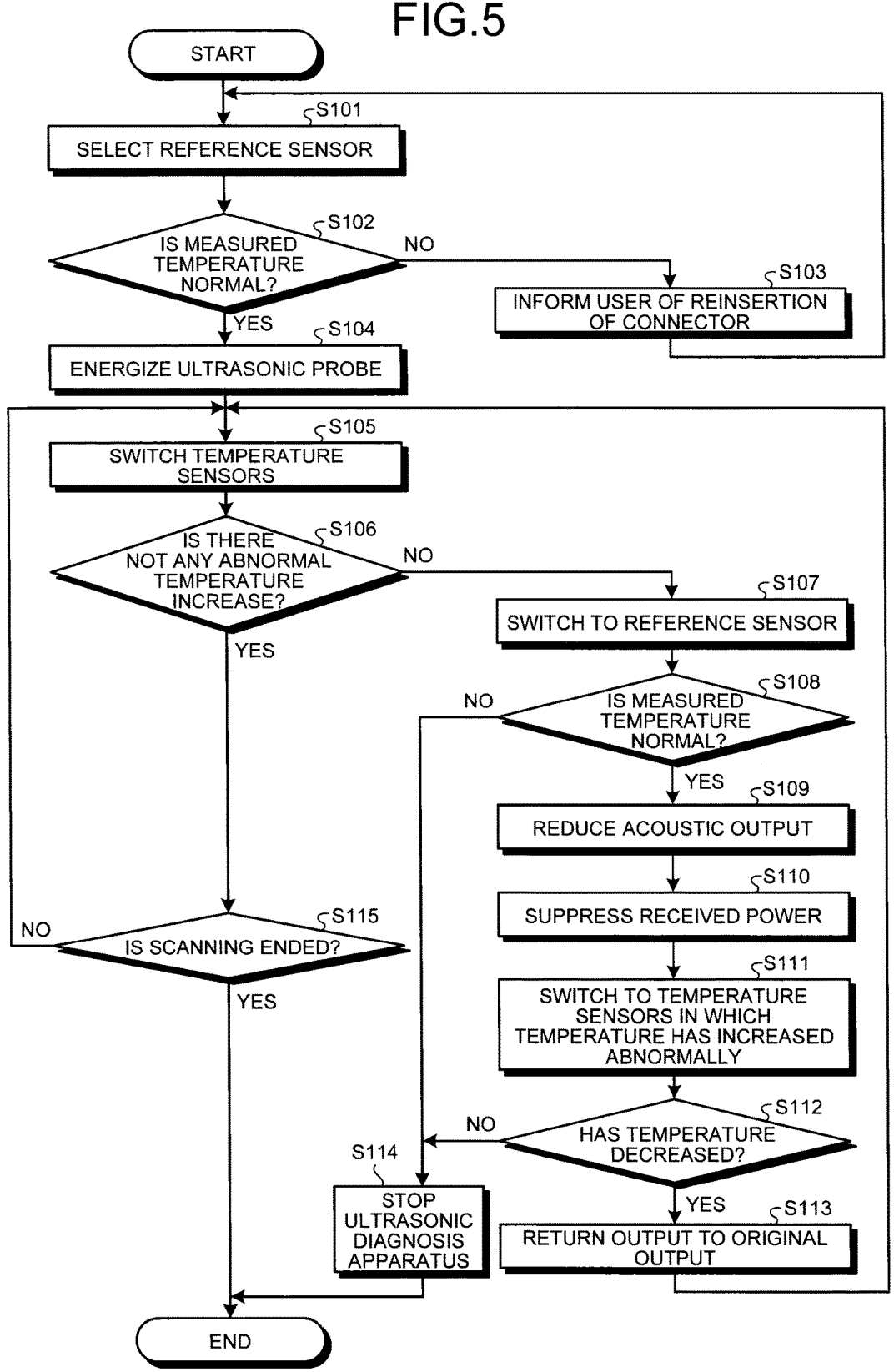
FIG. 5 is a flowchart of an example of a process procedure performed by the control unit according to the first embodiment.

Next, a process procedure performed by the control unit 40 is explained with reference to FIG. 5. FIG. 5 is a flowchart of an example of the process procedure performed by the control unit 40 according to the first embodiment.

When a target probe is connected to a main unit, the instruction unit 41 controls the switching circuit 59 to cause the switching circuit 59 to select the reference sensor 58 (Step S101). In a state where the reference sensor 58 is selected, the determination unit 42 determines whether a temperature measured by the temperature detector 30 is normal (Step S102).

When the determination unit 42 determines that the measured temperature is not normal (NO at Step S102), the determination unit 42 informs a user of reinsertion of a connector (Step S103), and the process proceeds to Step S101.

When it is determined that the measured temperature is not normal, the resistance value of a path increases due to a connection failure of a connector pin and a failure of a wire of the probe cable 3. As a result, the measured temperature is lower than a preset value. Therefore, the control unit 40 can recognize a failure of a temperature detection system of the ultrasonic probe 50 and inform the user of reinsertion of the connector. When an abnormality occurs repeatedly, the ultrasonic probe 50 can be energized to inform the user to prohibit the use thereof. The ultrasonic diagnosis apparatus 1 can thus maintain the safety of a subject.

When the reference sensor 58 is selected and measurement is performed, for example, there is a case where a slightly increased resistance value in which the difference between a resistance value of the reference sensor 58 and an expected value is $1.2\Omega$ and the like is measured repeatedly and stably. In such a case, the use of the ultrasonic probe 50 can be started after the resistance value of each sensor is corrected using an increase in the resistance. In this case, it is desirable to start using the ultrasonic probe 50 after displaying a caution for the user and correcting temperature detection.

When the determination unit 42 determines that the measured temperature is normal (YES at Step S102), the determination unit 42 energizes the ultrasonic probe 50 (Step S104). The ultrasonic diagnosis apparatus 1 thus starts to acquire image data. During a period in which the ultrasonic diagnosis apparatus 1 acquires image data, the instruction unit 41 instructs the switching circuit 59 to switch the temperature sensors 53 to 55 included in the acoustic module 51 at a fixed interval (Step S105).

The determination unit 42 then determines whether there is any abnormal temperature increase on a contact surface of the ultrasonic probe 50 with the subject (Step S106). When it is determined by the determination unit 42 that there is an abnormal temperature increase on the contact surface of the ultrasonic probe 50 with the subject (NO at Step S106), the instruction unit 41 instructs the switching circuit 59 to switch to the reference sensor 58 (Step S107). In such a case, for example, a power consumption operation can be temporarily stopped.

The determination unit 42 determines whether the temperature measured by the temperature detector 30 is normal (Step S108). When the determination unit 42 determines that the measured temperature is normal (YES at Step S108), the changing unit 43 reduces an acoustic output (Step S109) and suppresses received power (Step S110).

The instruction unit 41 then instructs the switching circuit 59 to switch to the temperature sensors 53 to 56 that are determined by the determination unit 42 that the temperature has increased abnormally (Step S111). In a state where an acoustic output is reduced and/or a state where power of the reception circuit 80 is suppressed, images are acquired and the determination unit 42 determines whether the temperature of the acoustic module 51 has decreased to a normal range (Step S112). When the ultrasonic probe 50 is under normal control, generally, the temperature decreases.

When the determination unit 42 determines that the temperature has decreased (YES at Step S112), the changing unit 43 returns the acoustic output level and the power of the reception circuit to the acoustic output level and the power of the reception circuit before the change (Step S113). After Step S113, the process proceeds to Step S105. In this way, the ultrasonic diagnosis apparatus 1 continues acquiring image data.

When the determination unit 42 determines at Step S108 that the measured temperature is not normal (NO at Step S108), the determination unit 42 causes the ultrasonic diagnosis apparatus 1 to stop acquisition of image data (Step S114), and the process ends. When the determination unit 42 determines at Step S112 that the temperature has not decreased (NO at Step S112), the determination unit 42 causes the ultrasonic diagnosis apparatus 1 to stop acquisition of image data (Step S114), and the process ends.

When the determination unit 42 determines at Step S106 that there is no abnormal temperature increase on the contact surface of the ultrasonic probe 50 with the subject (YES at Step S106), the control unit 40 determines whether the control unit 40 has acknowledged the end of scanning (Step S115).

When the control unit 40 determines that the control unit 40 has not acknowledged the end of scanning (NO at Step S115), the instruction unit 41 proceeds the process to Step S105, and instructs the switching circuit 59 to switch the temperature sensors 53 to 55. On the other hand, when the control unit 40 determines that the control unit 40 has acknowledged the end of scanning (YES at Step S115), the process ends.

In a case where when the power use state is returned to a normal level after the temperature has temporarily decreased, an abnormal temperature is detected in a short time, it can be determined that an abnormality occurs and use of the ultrasonic probe 50 can be stopped.

Furthermore, when a significant and abnormal temperature increase is detected in a very short time, it can be determined that there is an excessive and abnormal temperature increase due to an abnormality of a probe or control, and use of the ultrasonic probe 50 can be stopped.

As explained above, according to the first embodiment, the number of signal lines can be reduced. Therefore, by allocating wires of a probe cable and pins of probe connectors to a plurality of temperature sensors, it is possible to prevent the probe cable from becoming large and heavy. According to the first embodiment, even when the number of temperature sensors is increased, the operability of an ultrasonic probe can be maintained.

Figure 6:
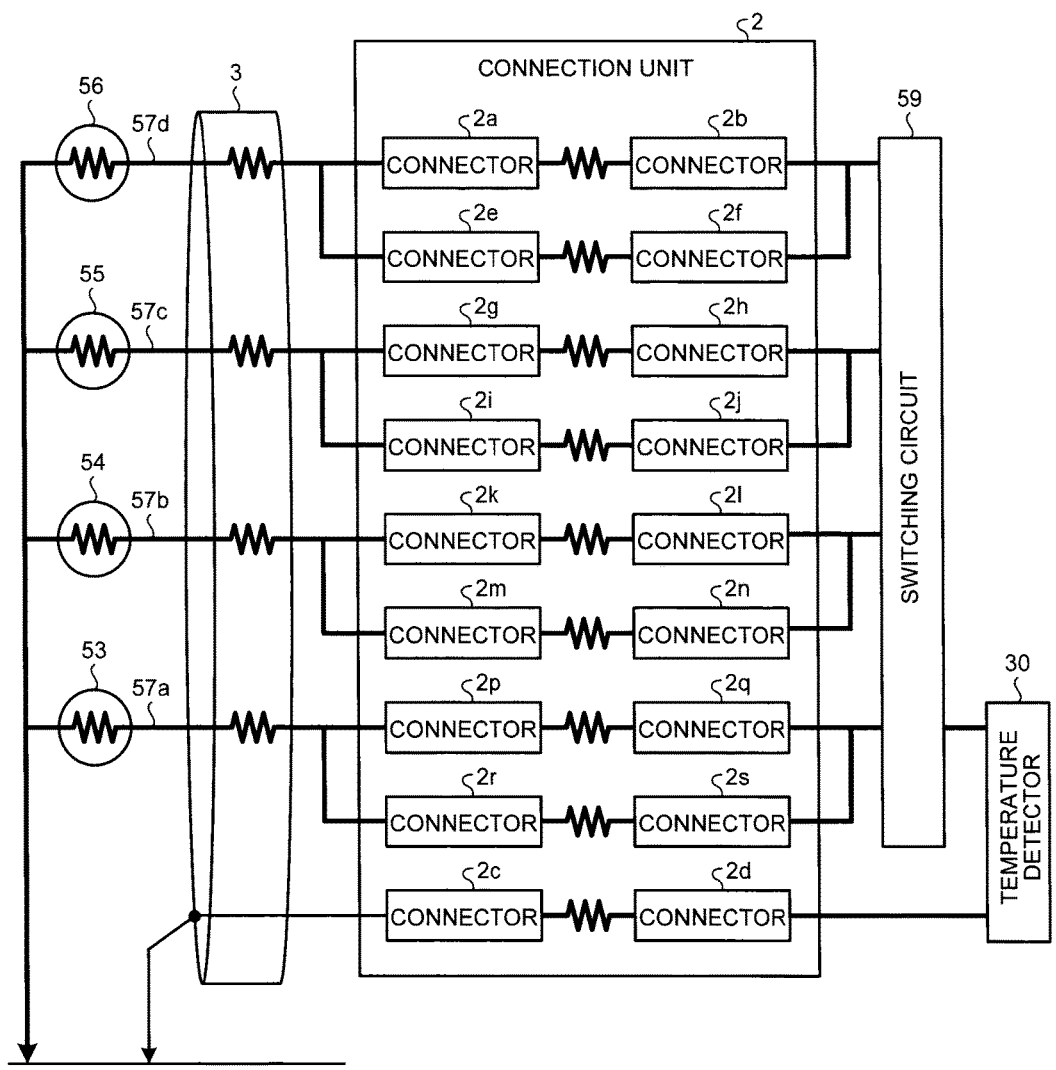
FIG. 6 is an example of a configuration of a probe cable and a connection unit when a switching circuit is not included in the ultrasonic probe and the number of temperature sensors is increased.

FIG. 6 is an example of a configuration of the probe cable 3 and the connection unit 2 when the switching circuit 59 is not included in the ultrasonic probe 50 and the number of temperature sensors is increased. Like constitution units as those shown in FIG. 4 are denoted by like reference signs.

In FIG. 6, the respective signal lines of the temperature sensors 53 to 56 are connected via the probe cable 3 to the connection unit 2. In the connection unit 2, the respective signal lines of the temperature sensors 53 to 56 are connected by connectors to the switching circuit 59 included in the ultrasonic-diagnosis-apparatus main unit 10. The signal lines from the temperature sensors 53 to 56 are made to be redundant and connected in parallel. Therefore, while there are four temperature sensors, there are nine connector pins in the connection unit 2. As explained above, by allocating wires of the probe cable 3 and pins of probe connectors to the respective temperature sensors, the probe cable 3 becomes large and heavy.

Meanwhile, according to the ultrasonic diagnosis apparatus of the first embodiment, the respective signal lines of the temperature sensors 53 to 56 are connected to the switching circuit 59, and only one sensor line 57 is allocated to the probe cable 3. Therefore, while there are four temperature sensors, there are four connectors in the connection unit 2. According to the ultrasonic diagnosis apparatus 1 of the first embodiment, it is possible to prevent the probe cable 3 from becoming large and heavy.

While the first embodiment has explained an example of temperature detection using a thermistor, even when other temperature detection elements are used, the same configuration can be realized. While an example of mounting the switching circuit 59 on the same substrate as transmission and reception circuits has been explained, even when the switching circuit 59 is mounted on a different substrate, identical effects can be achieved as long as a switch is provided on a side of a probe with respect to a probe cable connector.

An example of incorporating the electronic circuit 60 that relates to transmission and reception (the transmission circuit 70 and the reception circuit 80) in the ultrasonic probe 50 has been explained as the ultrasonic probe 50. However, even when a switching circuit of the temperature sensors 53 to 56 is configured in the ultrasonic probe 50 having only a switch that merely switches elements incorporated therein or in the ultrasonic probe 50 that does not include the electronic circuit 60 because the transmission circuit 70 and the reception circuit 80 are included in the ultrasonic-diagnosis-apparatus main unit 10, identical effects can be achieved. It is needless to say that not only the two-dimensionally arrayed ultrasonic probe 50 but also the one-dimensionally arrayed ultrasonic probe 50 can be applied.

The control unit 40 shown in FIGS. 1 and 4 can be configured so as to include the instruction unit 41 and the determination unit 42 but not the changing unit 43.

Second Embodiment

Figure 7:
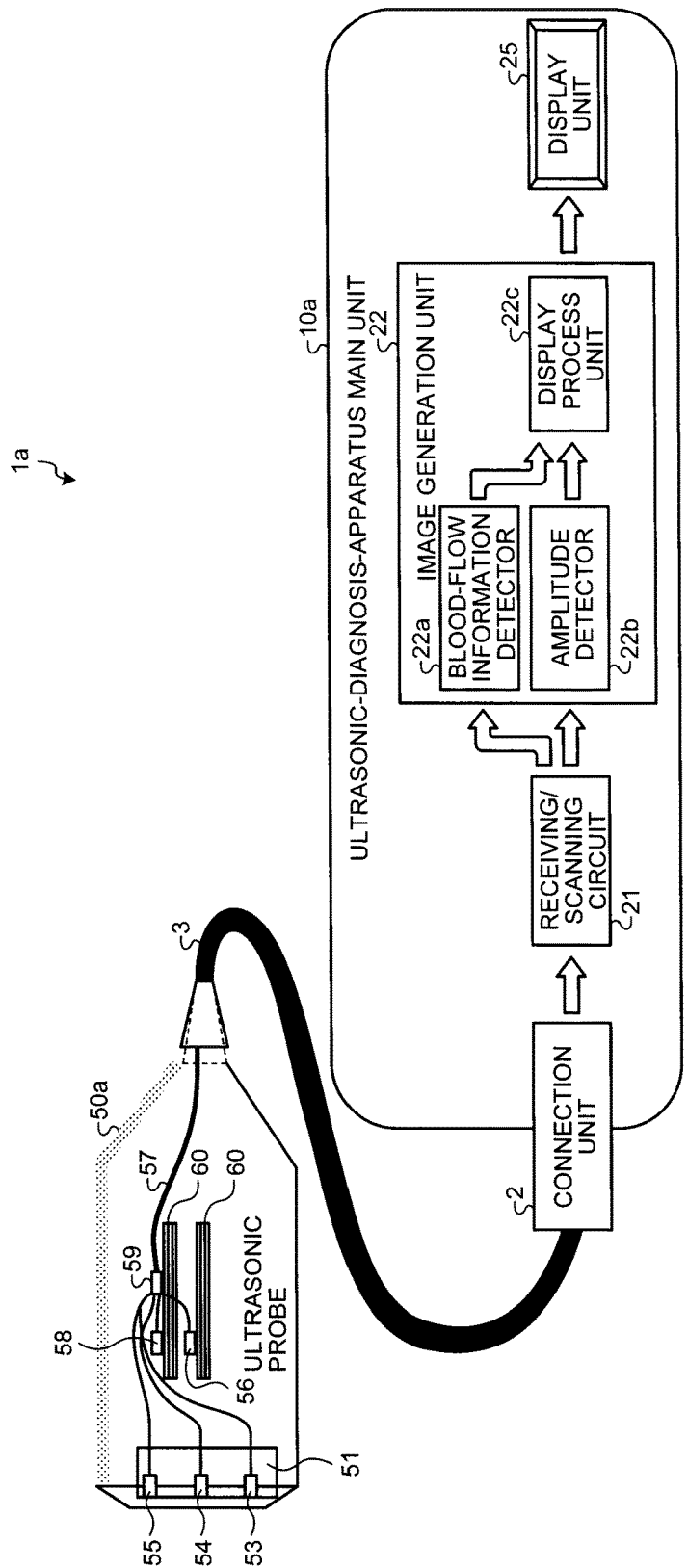
FIG. 7 is an example of a configuration of an ultrasonic diagnosis apparatus according to a second embodiment.

In a second embodiment, a case where the temperature detector 30 and the control unit 40 are included in the ultrasonic probe 50 is explained. FIG. 7 is an example of a configuration of an ultrasonic diagnosis apparatus 1a according to the second embodiment. As shown in FIG. 7, the ultrasonic diagnosis apparatus 1a according to the second embodiment includes an ultrasonic-diagnosis-apparatus main unit 10a and an ultrasonic probe 50a. Constituent elements identical to those of the respective elements shown in FIG. 1 are denoted by like reference signs and detailed explanations thereof will be omitted.

FIG. 7 is different from FIG. 1 such that the ultrasonic-diagnosis-apparatus main unit 10a does not include the temperature detector 30 and the control unit 40.

Figure 8:
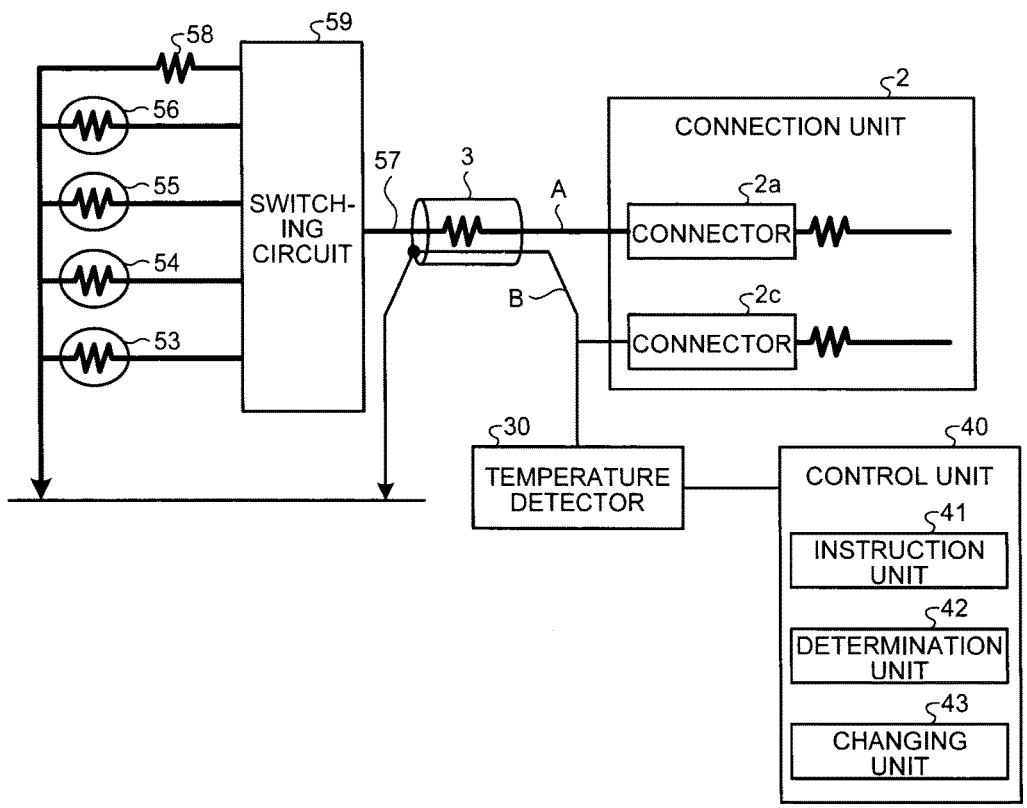
FIG. 8 is an explanatory diagram of an operation of a switching process of a sensor line by a control unit according to the second embodiment.

FIG. 8 is an explanatory diagram of an operation of a switching process of the sensor line 57 by the control unit 40 according to the second embodiment. Constituent elements identical to those of the respective elements shown in FIG. 4 are denoted by like reference signs and detailed explanations thereof will be omitted.

FIG. 8 is different from FIG. 4 such that a signal line to which signal lines of the temperature sensors 53 to 56 and the reference sensor 58 are commonly connected is connected to the temperature detector 30. The temperature detector 30 is connected to the control unit 40 within the ultrasonic probe 50.

In FIG. 8, when the reference sensor 58 is selected, a signal that is output by the switching circuit 59 to the sensor line 57 is input from the connection unit 2 via the ultrasonic-diagnosis-apparatus main unit 10a to the temperature detector 30. In FIG. 8, when any one of the temperature sensors 53 to 56 is selected, a signal that is output by the switching circuit 59 to the sensor line 57 is input via a path in which A and B in FIG. 8 are short-circuited by a switch (not shown) and the like to the temperature detector 30.

The ultrasonic diagnosis apparatus 1a can be also configured so that the ultrasonic probe 50 includes the temperature detector 30 and the ultrasonic-diagnosis-apparatus main unit 10a includes the control unit 40. Further, in the ultrasonic diagnosis apparatus 1a, the respective units included in the control unit 40 can be distributed to the ultrasonic probe 50 and the ultrasonic-diagnosis-apparatus main unit 10a. In the ultrasonic diagnosis apparatus 1a, functions included in the control unit 40 can be realized by an FPGA (Field-Programmable Gate Array) to reduce the weight of the ultrasonic diagnosis apparatus 1a.

The control unit 40 shown in FIG. 8 can be configured so as to include the instruction unit 41 and the determination unit 42 but not the changing unit 43.

As explained above, according to the second embodiment, the number of signal lines can be reduced. Therefore, by allocating wires of a probe cable and pins of probe connectors to a plurality of temperature sensors, it is possible to prevent the probe cable from becoming large and heavy. Therefore, according to the second embodiment, even when the number of temperature sensors is increased, the operability of an ultrasonic probe can be maintained.

Third Embodiment

In the above embodiments, a case where connection to any one of temperature sensors is switched to a valid state in a predetermined order has been explained. According to these embodiments, temperature sensors are switched at a predetermined time interval. In a third embodiment, control of the timing of switching temperature sensors is explained in detail.

Basically, a temperature sensor is incorporated in the acoustic module 51 to prevent a subject from having a burn when the temperature of the acoustic module 51 is abnormal. Therefore, it is desirable to design control of transmission and reception of ultrasonic waves and control of switching of temperature sensors independently from each other so that even when an abnormality occurs in control of transmission and reception of the ultrasonic diagnosis apparatus 1, a temperature abnormality is detectable. For example, in a case where the control of transmission and reception of ultrasonic waves cooperates with the control of switching of temperature sensors, when an abnormality occurs in the control of transmission and reception, there is a possibility that a temperature abnormality cannot be detected. For example, the case where the control of transmission and reception of ultrasonic waves cooperates with the control of switching of temperature sensors refers to a case where, depending on ultrasonic transducer elements driven by scanning, connection to a temperature sensor that is installed near these ultrasonic transducer elements is switched to a valid state.

Specifically, in a case where control of transmission and reception of ultrasonic waves cooperates with control of switching of temperature sensors and some ultrasonic transducer elements "a" within the ultrasonic probe 50 are driven, when an abnormality occurs in the transmission circuit 70, in practice, some other ultrasonic transducer elements "b" may be driven even though the ultrasonic transducer elements "a" are intended to be driven. In this case, the temperatures of the ultrasonic transducer elements "b" sometimes increase. However, because the instruction unit 41 switches to a temperature sensor that cooperates with the ultrasonic transducer elements "a", the temperatures of the ultrasonic transducer elements "b" cannot be measured. Accordingly, when the control of transmission and reception of ultrasonic waves cooperates with the control of switching of temperature sensors, because control of transmission and reception of the ultrasonic diagnosis apparatus 1 itself is inaccurate, an abnormality in the temperature of ultrasonic transducer elements cannot be detected.

Accordingly, an ultrasonic diagnosis apparatus 1b according to the third embodiment executes control of transmission and reception of ultrasonic waves and control of temperature sensors independently. The ultrasonic diagnosis apparatus 1b according to the third embodiment switches temperature sensors at a timing at which a temperature abnormality can be detected at a predetermined time interval. A configuration of the ultrasonic diagnosis apparatus 1b according to the third embodiment is the same as that of the ultrasonic diagnosis apparatus 1 shown in FIG. 1 except that a part of functions of the instruction unit 41 and the determination unit 42 is different. Therefore, detailed explanations of functional units other than the instruction unit 41 and the determination unit 42 according to the third embodiment will be omitted.

The instruction unit 41 according to the third embodiment instructs the switching circuit 59 to switch connection to any one of a plurality of temperature sensors to a valid state at a predetermined time interval. For example, the instruction unit 41 outputs a switching signal that instructs the switching circuit 59 to switch connection to any one of the temperature sensors to a valid state to the switching circuit 59 at every predetermined time interval. The instruction unit 41 outputs a switching signal to the switching circuit 59 at a timing at which a temperature sensor can measure the temperature and detect a temperature abnormality at an appropriate time interval.

Figure 9:
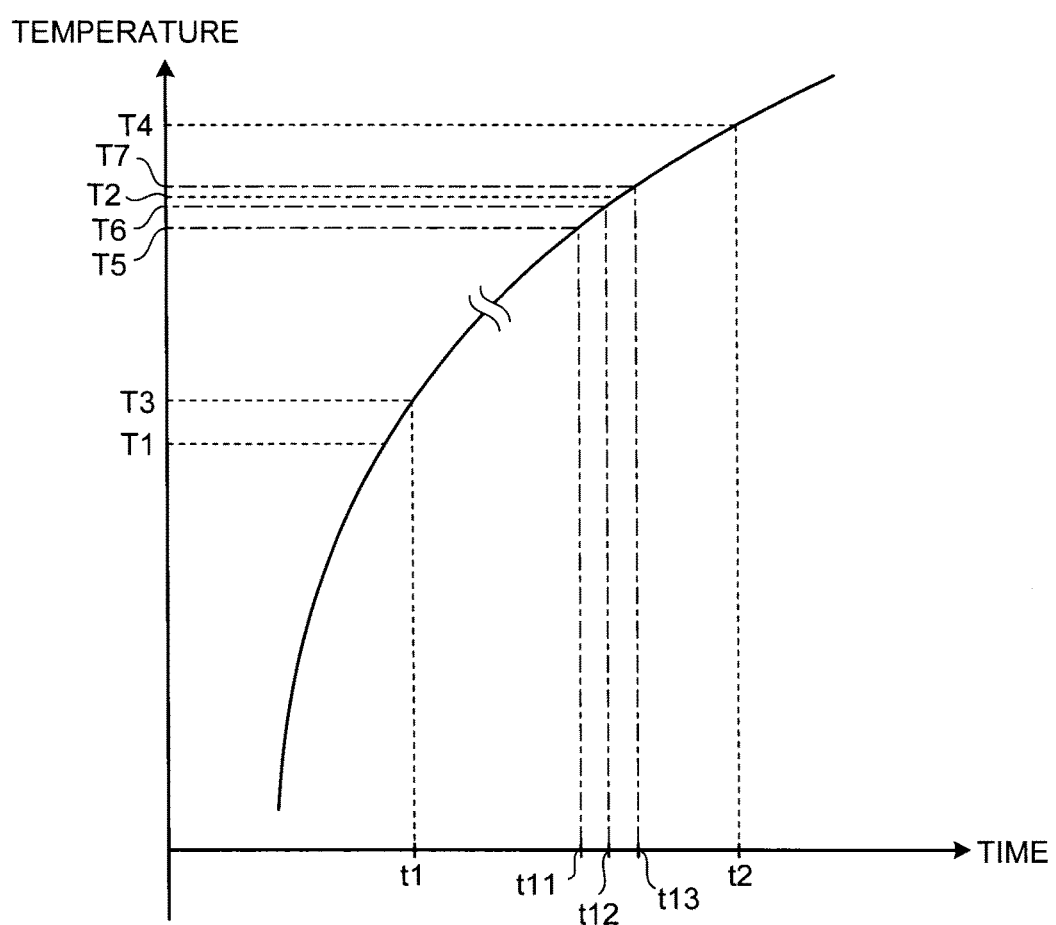
FIG. 9 is an explanatory diagram of a process operation performed by an instruction unit according to a third embodiment.

A process operation performed by the instruction unit 41 according to the third embodiment is explained in detail below. FIG. 9 is an explanatory diagram of the process operation performed by the instruction unit 41 according to the third embodiment. FIG. 9 depicts a change in the temperature of an ultrasonic transducer element according to an elapsed time. In FIG. 9, the vertical axis indicates the temperature of an ultrasonic transducer element that is measured by a temperature sensor, and the horizontal axis indicates time. A change in the temperature of an ultrasonic transducer element according to an elapsed time shown in FIG. 9 (hereinafter, also "temperature increase speed") is determined based on "heat capacity of ultrasonic transducer element" and "transmitted and received ultrasonic energy". "Heat capacity of ultrasonic transducer element" is determined based on at least one of the material of the ultrasonic probe 50 and the thickness thereof. Further, it is assumed that the maximum value of energy available from the ultrasonic diagnosis apparatus 1b is "transmitted and received ultrasonic energy". Therefore, the instruction unit 41 according to the third embodiment calculates a temperature increase speed in advance from at least one of the material and thickness of the ultrasonic probe 50 and the maximum value of energy available from the ultrasonic diagnosis apparatus 1b. The instruction unit 41 according to the third embodiment can hold the temperature increase speed derived in advance.

The instruction unit 41 determines a predetermined time interval of instructing the switching circuit 59 to switch connection to any one of temperature sensors to a valid state based on the temperature increase speed. It suffices that the instruction unit 41 determines a time interval during which a fact that the temperature is increasing can be detected. For example, it suffices that the instruction unit 41 determines a predetermined time interval so that temperature sensors are switched at a timing faster than a temperature increase as shown in FIG. 9. It is assumed that the range between a temperature T1 and a temperature T2 shown in FIG. 9 is a set temperature range in the ultrasonic diagnosis apparatus 1b. This set temperature range is a temperature range that is safe for a subject. The instruction unit 41 determines a time interval so that the temperature is measured for a fixed number of times within the set temperature range. For example, this time interval is desirably an interval during which a curve of a temperature increase (degree of a temperature increase) is detected in the middle of the increase within the set temperature range. In FIG. 9, a case where the ultrasonic diagnosis apparatus 1b captures a fixed area at the maximum value of available energy at a cycle of 30 milliseconds is explained. In FIG. 9, a case where the number of temperature sensors is three is also explained.

For example, when measurement starts at t1 shown in FIG. 9 using a temperature sensor A, a temperature T3 at t1 is within the set temperature range. For example, when it is assumed that a temperature measured by the temperature sensor A at t2 after 30 milliseconds from t1 is indicated as T4, T4 is out of the set temperature range. In a case where a time interval is set so that after the temperature is measured at t1, the temperature is measured at t2, even when the temperature T3 measured at t1 is within the set temperature range, the temperature T4 measured at t2 may no longer be within the set temperature range.

Therefore, as shown in FIG. 9, the instruction unit 41 determines a time interval of switching temperature sensors so that each temperature sensor measures the temperature for 1000 times per second. That is, in the ultrasonic diagnosis apparatus 1b, the instruction unit 41 switches temperature sensors for every 0.3 milliseconds and the temperature is measured by each temperature sensor. According to an example shown in FIG. 9, the temperature starts to be measured at t1 and is measured by the temperature sensor A for every millisecond. In the ultrasonic diagnosis apparatus 1b, the temperature is measured by three temperature sensors for 3,000 times in total per second. For example, as shown in FIG. 9, after the temperature starts to be measured at t1 by the temperature sensor A, the temperature is measured by the temperature sensor A for every millisecond. When it is assumed that a temperature measured by the temperature sensor A at t11 is indicated as T5, this temperature T5 is within the set temperature range. Further, when it is assumed that a temperature measured by the temperature sensor A at t12 after a millisecond from t11 is indicated as T6, this temperature T6 is also within the set temperature range. On the other hand, when it is assumed that a temperature measured by the temperature sensor A at t13 after a millisecond from t12 is indicated as T7, the temperature T7 is out of the set temperature range. As explained above, the instruction unit 41 outputs a switching signal that instructs the switching circuit 59 to switch connection to any one of temperature sensors to a valid state at a time interval during which a curve of a temperature increase (the degree of a temperature increase) is detected in the middle of the increase within the set temperature range to the switching circuit 59. Accordingly, even when capturing is performed at the maximum value of energy available from the ultrasonic diagnosis apparatus 1b, it is possible to detect whether the ultrasonic probe 50 is within the set temperature range.

When it is instructed to switch temperature sensors at a timing at which the reception circuit 80 receives a reflected wave signal, a switching signal is input to the reception circuit 80. That is, by switching the temperature sensors by the instruction unit 41, electric noise is input to the reception circuit 80. In such a case, a bright point is formed at a position of an ultrasonic image where a reflector is not present. Therefore, the instruction unit 41 adjusts a timing so as not to instruct the switching circuit 59 to switch temperature sensors during a period in which the reception circuit 80 receives a reflected wave signal. For example, the instruction unit 41 instructs the switching circuit 59 to switch temperature sensors at a timing at which an ultrasonic wave is transmitted.

At Step S105 shown in FIG. 5, during a period in which the ultrasonic diagnosis apparatus 1b acquires image data, the instruction unit 41 according to the third embodiment instructs the switching circuit 59 to switch the temperature sensors 53 to 55 included in the acoustic module 51 at a predetermined time interval. While the third embodiment has explained that the instruction unit 41 determines the time interval, the embodiment is not limited thereto. For example, the instruction unit 41 according to the third embodiment can be configured so as to hold a time interval derived in advance and output a switching signal that instructs the switching circuit 59 to switch connection to any one of a plurality of temperature sensors to a valid state to the switching circuit 59 at this timer interval.

As explained above, the ultrasonic diagnosis apparatus 1b according to the third embodiment executes control of transmission and reception of ultrasonic waves and control of temperature sensors independently, and instructs the switching circuit 59 to switch connection to any one of temperature sensors to a valid state at a predetermined time interval. According to the third embodiment, it is possible to detect a fact that the temperature is increasing within a set temperature range.

On the other hand, when the control of transmission and reception of ultrasonic waves cooperates with the control of switching of temperature sensors, as a capturing cycle becomes longer, it becomes more difficult to appropriately switch the temperature sensors. For example, when an ultrasonic diagnosis apparatus acquires Doppler image information, the ultrasonic diagnosis apparatus captures the same portion to acquire an average speed (or the maximum speed), a speed distribution (or a speed distribution width), scattering power information from a blood flow, and the like. For this reason, to acquire Doppler image information, the ultrasonic diagnosis apparatus captures a fixed area at a cycle of, for example, 100 milliseconds. In such a case, when control of transmission and reception of ultrasonic waves cooperates with control of switching of temperature sensors, a timing of switching the temperature sensors becomes slower and it may be impossible to detect a temperature increase. Accordingly, when the control of transmission and reception of ultrasonic waves cooperates with the control of switching of temperature sensors, it may be impossible to detect a fact that the temperature is increasing.

Furthermore, because an update speed is slow in three-dimensional scanning, the number of captures per second may be one or two. In such three-dimensional scanning, when control of transmission and reception of ultrasonic waves cooperates with control of switching of temperature sensors, a timing of switching the temperature sensors becomes slower than a timing when Doppler image information is an observation target, and it is impossible to detect a temperature increase.

In the above embodiments, while a case where temperature sensors are arranged in a line has been explained, the embodiments are not limited thereto. For example, temperature sensors can be arranged in multiple lines, for example, three lines.

Other Embodiments

The determination unit 42 can be configured so as to determine that the temperature of the ultrasonic probe 50 is abnormal when a temperature measured by the temperature detector 30 is out of a set temperature range. Also in such a case, the ultrasonic diagnosis apparatus 1b can further determine whether a connection state between connectors of the connection unit 2 is normal. For example, when it is determined by the determination unit 42 that a temperature measured by a temperature sensor whose connection is in a valid state is out of the set temperature range, the instruction unit 41 instructs the switching circuit 59 to switch connection to the reference sensor 58 to a valid state. When connection to the reference sensor 58 is in a valid state and connection of the temperature detector 30 and the control unit 40 is normal, the determination unit 42 determines that the temperature of the ultrasonic probe 50 is abnormal.

By switching the temperature sensors at a predetermined time interval, the determination unit 42 can detect a fact that the temperature is increasing within the set temperature range. For example, when a temperature measured by the temperature detector 30 is within the set temperature range and the difference between this temperature and a previously measured temperature is equal to or larger than a predetermined threshold, the determination unit 42 can determine that the temperature of the ultrasonic probe 50 is abnormal. Therefore, for example, even when the temperature changes rapidly, the ultrasonic diagnosis apparatus 1b can prevent a subject from having a burn. Also in such a case, the ultrasonic diagnosis apparatus 1b can further determine whether a connection state between connectors of the connection unit 2 is normal. For example, when it is determined by the determination unit 42 that the difference between a measured temperature and a previously measured temperature is equal to or larger than a predetermined threshold, the instruction unit 41 instructs the switching circuit 59 to switch connection to the reference sensor 58 to a valid state. When connection to the reference sensor 58 is in a valid state and connection of the temperature detector 30 and the control unit 40 is normal, the determination unit 42 determines that the temperature of the ultrasonic probe 50 is abnormal.

For example, when a temperature measured by the temperature detector 30 is within the set temperature range but the temperature continuously increases for a predetermined period, before the temperature is out of the set temperature range, the determination unit 42 can determine that the temperature of the ultrasonic probe 50 is abnormal. Therefore, for example, even when the temperature continuously increases, the ultrasonic diagnosis apparatus 1b can prevent a subject from having a burn. Also in such a case, the ultrasonic diagnosis apparatus 1b can further determine whether a connection state between connectors of the connection unit 2 is normal. For example, when it is determined by the determination unit 42 that the temperature continuously increases for a predetermined period, the instruction unit 41 instructs the switching circuit 59 to switch connection to the reference sensor 58 to a valid state. When connection to the reference sensor 58 is in a valid state and connection of the temperature detector 30 and the control unit 40 is normal, the determination unit 42 determines that the temperature of the ultrasonic probe 50 is abnormal.

According to at least one of the embodiments explained above, even when the number of temperature sensors is increased, the operability of the ultrasonic probe can be maintained.

Although several embodiments of the present invention have been explained above, these embodiments are presented as illustrative examples, and the scope of the invention is not intended to be limited thereto. These embodiments can be also carried out by various other modes, and various omissions, replacements, and changes can be made without departing from the scope of the invention. Such embodiments and modifications thereof are included in the spirit and scope of the invention and are also included in the scope of the inventions described in the claims as well as in equivalents thereof.

What is claimed is:

1. An ultrasonic diagnosis apparatus, comprising:
an ultrasonic probe that transmits and receives an ultrasonic wave to and from a subject;
image generation circuitry that generates image data from a reflected wave received from the ultrasonic probe;
a display that displays the generated image data; and
control circuitry that controls transmission and reception of the ultrasonic wave by the ultrasonic probe, wherein
the ultrasonic probe includes a plurality of temperature sensors that are installed at a plurality of positions within the ultrasonic probe, and a switching circuit that is connected to the respective temperature sensors and switches a connection to any one of the temperature sensors to an on state to successively output data from the respective temperature sensors to a temperature detector that measures a temperature using output data of the temperature sensors, and
the control circuitry further includes instruction circuitry that instructs the switching circuit to switch the connection to any one of the temperature sensors to the on state at a predetermined time interval, and determination circuitry that determines whether a temperature measured by the temperature detector is within a set temperature range.

2. The ultrasonic diagnosis apparatus according to claim 1, wherein the instruction circuitry further instructs the switching circuit to switch the connection to one of the temperature sensors to the on state at the predetermined time interval that is determined based on a rate of temperature increase.

3. The ultrasonic diagnosis apparatus according to claim 2, wherein the rate of temperature increase is derived based on at least one of a material and a thickness of the ultrasonic probe and transmitted and received ultrasonic energy.

4. The ultrasonic diagnosis apparatus according to claim 1, wherein
the ultrasonic probe further includes a reference sensor that outputs data for the temperature detector to detect whether a connection of the temperature detector and the control circuitry is normal,
the switching circuit is further connected to the reference sensor and switches the connection to any one of the temperature sensors and the reference sensor to the on state to successively output output data of the respective sensors to the temperature detector,
the instruction circuitry further instructs the switching circuit to switch the connection to any one of the temperature sensors and the reference sensor to the on state at the predetermined time interval, and
when the connection to the reference sensor is in the on state and the connection of the temperature detector and the control circuitry is normal, the determination circuitry permits the instruction circuitry to switch the connection to any one of the temperature sensors to the on state.

5. The ultrasonic diagnosis apparatus according to claim 2, wherein
the ultrasonic probe further includes a reference sensor that outputs data for the temperature detector to detect whether a connection of the temperature detector and the control circuitry is normal,
the switching circuit is further connected to the reference sensor and switches the connection to any one of the temperature sensors and the reference sensor to the on state to successively output output data of the respective sensors to the temperature detector, the instruction circuitry further instructs the switching circuit to switch the connection to any one of the temperature sensors and the reference sensor to the on state at the predetermined time interval, and when the connection to the reference sensor is in the on state and the connection of the temperature detector and the control circuitry is normal, the determination circuitry permits the instruction circuitry to switch the connection to any one of the temperature sensors to the on state.

6. The ultrasonic diagnosis apparatus according to claim 3, wherein the ultrasonic probe further includes a reference sensor that outputs data for the temperature detector to detect whether a connection of the temperature detector and the control circuitry is normal, the switching circuit is further connected to the reference sensor and switches the connection to any one of the temperature sensors and the reference sensor to the on state to successively output output data of the respective sensors to the temperature detector, the instruction circuitry instructs the switching circuit to switch the connection to any one of the temperature sensors and the reference sensor to the on state at the predetermined time interval, and when the connection to the reference sensor is in the on state and the connection of the temperature detector and the control circuitry is normal, the determination circuitry permits the instruction circuitry to switch the connection to any one of the temperature sensors to the on state.

7. The ultrasonic diagnosis apparatus according to claim 1, wherein when a temperature measured by the temperature detector is out of the set temperature range, the determination circuitry stops transmission and reception of the ultrasonic wave.

8. The ultrasonic diagnosis apparatus according to claim 1, wherein when a temperature measured by the temperature detector is within the set temperature range and a difference between the temperature and a previously measured temperature is equal to or larger than a predetermined threshold, the determination circuitry stops transmission and reception of the ultrasonic wave.

9. The ultrasonic diagnosis apparatus according to claim 1, wherein when a temperature measured by the temperature detector is within the set temperature range and a temperature continuously increases for a predetermined period, the determination circuitry stops transmission and reception of the ultrasonic wave.

10. The ultrasonic diagnosis apparatus according to claim 4, wherein when it is determined by the determination circuitry that a temperature measured by the temperature sensor whose connection is in the on state is out of the set temperature range, the instruction circuitry instructs the switching circuit to switch the connection to the reference sensor to the on state, and when the connection to the reference sensor is in the on state and the connection of the temperature detector and the control circuitry is normal, the determination circuitry stops transmission and reception of the ultrasonic wave.

11. The ultrasonic diagnosis apparatus according to claim 4, wherein when it is determined by the determination circuitry that a temperature measured by the temperature detector is within the set temperature range and a difference between the temperature and a previously measured temperature is equal to or larger than a predetermined threshold, the instruction circuitry instructs the switching circuit to switch the connection to the reference sensor to the on state, and when the connection to the reference sensor is in the on state and the connection of the temperature detector and the control circuitry is normal, the determination circuitry stops transmission and reception of the ultrasonic wave.

12. The ultrasonic diagnosis apparatus according to claim 4, wherein when it is determined by the determination circuitry that a temperature measured by the temperature detector is within the set temperature range and a temperature continuously increases for a predetermined period, the instruction circuitry instructs the switching circuit to switch the connection to the reference sensor to the on state, and when the connection to the reference sensor is in the state and the connection of the temperature detector and the control circuitry is normal, the determination circuitry stops transmission and reception of the ultrasonic wave.

13. The ultrasonic diagnosis apparatus according to claim 1, wherein when a temperature measured by the temperature detector is out of the set temperature range, the determination circuitry informs a user that the temperature of the ultrasonic probe is out of the set temperature range.

14. The ultrasonic diagnosis apparatus according to claim 1, wherein when a temperature measured by the temperature detector is out of the set temperature range, the determination circuitry stops use of the ultrasonic probe.

15. The ultrasonic diagnosis apparatus according to claim 1, further comprising changing circuitry that, when the temperature measured by the temperature detector is within the set temperature range, reduces power consumption of the ultrasonic diagnosis apparatus more than power consumption at a time when a temperature measured by the temperature detector is out of the set temperature range.

16. The ultrasonic diagnosis apparatus according to claim 15, wherein after a process of reducing power consumption is performed by the changing circuitry, when connection to the temperature sensor is in the on state and a temperature measured by the temperature sensor is within the set temperature range, the determination circuitry determines that diagnosis by the ultrasonic diagnosis apparatus can be performed, and when it is determined by the determination circuitry that diagnosis by the ultrasonic diagnosis apparatus can be performed, the changing circuitry changes the reduced power consumption to power consumption before the reduction.

17. The ultrasonic diagnosis apparatus according to claim 1, wherein one ends of signal lines of the temperature sensors are connected to the switching circuit and other ends of the signal lines of the temperature sensors are commonly connected to a ground.

18. The ultrasonic diagnosis apparatus according to claim 1, wherein the temperature sensors are constituted by a plurality of first temperature sensors that are installed at a plurality of positions of an acoustic module included in the ultrasonic probe, and
at least one second temperature sensor that is installed in an electronic circuit included in the ultrasonic probe.

19. The ultrasonic diagnosis apparatus according to claim 1, wherein the temperature sensor is a thermistor.

* * * * *